(12) United States Patent
Kamei

(10) Patent No.: US 8,026,330 B2
(45) Date of Patent: Sep. 27, 2011

(54) ORGANOPOLYSILOXANE HAVING CARBOXYL GROUPS

(75) Inventor: Masanao Kamei, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 266 days.

(21) Appl. No.: 12/417,403

(22) Filed: Apr. 2, 2009

(65) Prior Publication Data

US 2009/0253885 A1 Oct. 8, 2009

(30) Foreign Application Priority Data

Apr. 3, 2008 (JP) ................................. 2008-097561
Mar. 25, 2009 (JP) ................................. 2009-073665

(51) Int. Cl.
*C08G 77/04* (2006.01)
(52) U.S. Cl. ........................................................ 528/26
(58) Field of Classification Search ........................ None
See application file for complete search history.

(56) References Cited

U.S. PATENT DOCUMENTS

| | | | | |
|---|---|---|---|---|
| 4,486,405 | A | | 12/1984 | Klein |
| 4,598,135 | A | * | 7/1986 | Buese ............................... 528/23 |
| 4,876,152 | A | * | 10/1989 | Kang ............................ 428/447 |
| 4,935,332 | A | * | 6/1990 | Lauke et al. ................ 430/272.1 |
| 5,063,052 | A | * | 11/1991 | Grollier et al. ............. 424/70.121 |
| 5,385,999 | A | * | 1/1995 | D'Anvers et al. ................ 528/21 |
| 5,470,910 | A | * | 11/1995 | Spanhel et al. ................ 524/785 |
| 5,536,304 | A | * | 7/1996 | Coppens et al. ............. 252/8.57 |
| 6,103,222 | A | | 8/2000 | Goldsworthy et al. |
| 6,184,329 | B1 | * | 2/2001 | Jost et al. ........................... 528/15 |
| 6,491,981 | B1 | * | 12/2002 | Guichard et al. .............. 427/387 |
| 6,592,854 | B1 | | 7/2003 | Dupuis |
| 2002/0028899 | A1 | | 3/2002 | Breunig et al. ................. 528/10 |
| 2003/0211057 | A1 | * | 11/2003 | Majeti et al. ..................... 424/59 |
| 2003/0212231 | A1 | * | 11/2003 | Olier ................................. 528/10 |
| 2003/0212232 | A1 | * | 11/2003 | Majeti et al. ..................... 528/10 |
| 2005/0250904 | A1 | * | 11/2005 | Okawa et al. ................ 525/54.2 |

FOREIGN PATENT DOCUMENTS

| | | | |
|---|---|---|---|
| AT | 503652 | * | 12/2007 |
| DE | 19822618 | * | 2/2000 |
| JP | 2002-114849 A | | 4/2002 |
| WO | WO-96/32432 A1 | | 10/1996 |
| WO | WO-03/094871 A1 | | 11/2003 |
| WO | WO-03/095530 A1 | | 11/2003 |

OTHER PUBLICATIONS

The European Search Report for EP Appl. No. 09 25 1038.7, dated Jun. 16, 2009.

* cited by examiner

*Primary Examiner* — Robert Loewe
(74) *Attorney, Agent, or Firm* — Birch, Stewart, Kolasch & Birch, LLP

(57) ABSTRACT

An organopolysiloxane represented by the following average compositional formula (1):

$$R^1_a R^2_b R^3_c SiO_{(4-a-b-c)/2} \qquad (1)$$

wherein $R^1$ is selected from the group consisting of C1-30 alkyl, C1-30 fluoroalkyl, C6-30 aryl, and C6-30 aralkyl groups,
$R^2$ is a group represented by the following formula (2), provided that $R^2$ is bonded to at least one terminal end of the organopolysiloxane when c equals 0,

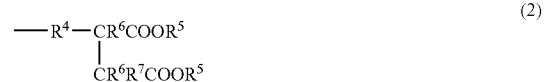

$R^3$ is a group represented by the following formula (3):

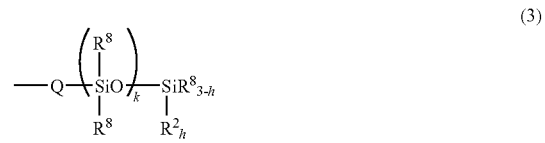

wherein $R^2$ is as defined above, each $R^8$ is, independently, selected from the group consisting of C1-30 alkyl, C1-30 fluoroalkyl, C6-30 aryl, and C6-30 aralkyl groups, Q is $C_d H_{2d}$ or an oxygen atom, wherein d is an integer of from 1 to 5, k is an integer of from 0 to 500, and h is an integer of from 0 to 3,
a is a number of from 1.5 to 2.5,
b is a number of from 0.001 to 1.5, and
c is a number of from 0 to 1.5.

7 Claims, No Drawings

ORGANOPOLYSILOXANE HAVING CARBOXYL GROUPS

CROSS REFERENCES

This application claims benefits of Japanese Patent Application No. 2008-097561 filed on Apr. 3, 2008, and No. 2009-73665 filed on Mar. 25, 2009, the contents of which are hereby incorporated by reference.

FIELD OF THE INVENTION

The present invention relates to an organopolysiloxane having carboxyl groups, specifically to an organopolysiloxane having two carboxyl groups per silicon atom. The organopolysiloxane has high reactivity with various kinds of substrates and affinity with unctuous agents.

BACKGROUND OF THE INVENTION

Organopolysiloxanes are used in various industrial fields such as electric, electrical, automobile, office automation equipment, medical care, cosmetic, food, and architecture industries. According to requirements and usages in each of the fields, organopolysiloxanes having various kinds of organic substituent groups have been developed. An organopolysiloxane having a carboxyl group or its salts, hereinafter collectively referred to as "carboxyl group", has been also developed for the reason that the carboxyl group is useful for surface-treating fibers, paper, human hair and inorganic fillers because of its functionalities such as reactivity and electrolytic property.

For example, an organopolysiloxanes having the following carboxyl group is known.

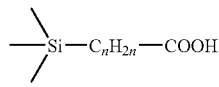

WO 96/32432 A1 describes an organopolysiloxane having the following group:

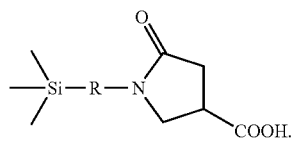

JP 2002-114849A describes an organopolysiloxane having either of the following groups:

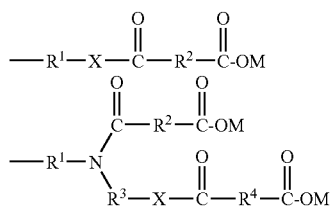

wherein X is —O— or —NH—, M is a hydrogen atom, metal, ammonium or the like.

U.S. Pat. No 6,592,854 B1 describes an organopolysiloxane having the following groups:

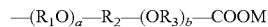

wherein M is a hydrogen atom, alkali metal, ammonium or the like.

WO 03/095530 A1 and WO 03/094871 A1 describe an organopolysiloxane having the following group:

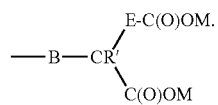

In the above organopolysiloxanes, the first three organopolysiloxanes have only one carboxyl group bonded to a silicon atom. The fourth organopolysiloxane has two carboxyl groups per silicon atom. However, it has a drawback that it has to be prepared from a special organopolysiloxane having two terminal amino groups or a special organopolysiloxane having an amino group and a hydroxyl group. The fifth organopolysiloxane is relatively easy to prepare. However, its affinity with unctuous agents such as hydrocarbon unctuous agent is not satisfactory.

SUMMARY OF THE INVENTION

An object of the present invention is therefore to provide an organopolysiloxane which has two carboxyl groups bonded to a silicon atom and has highly reactive carboxyl groups and affinity with unctuous agents.

The present invention is an organopolysiloxane represented by the following average compositional formula (1):

$$R^1_a R^2_b R^3_c SiO_{(4-a-b-c)/2} \qquad (1)$$

wherein $R^1$ is selected from the group consisting of C1-30 alkyl, C1-30 fluoroalkyl, C6-30 aryl, and C6-30 aralkyl groups, $R^2$ is a group represented by the following formula (2), provided that $R^2$ is bonded to at least one terminal end of the organopolysiloxane when c equals 0,

wherein $R^4$ is a C2-20 divalent hydrocarbon group which has an oxygen atom or no oxygen atom, each $R^5$ is, independently, a hydrogen atom, a monovalent cation, or a C1-10 alkyl group, provided that at least one of $R^5$'s is a hydrogen atom or a monovalent cation, each $R^6$ is, independently, a hydrogen atom or a C1-6 alkyl group, and $R^7$ is a hydrogen atom or a C1-6 alkyl group, $R^3$ is a group represented by the following formula (3):

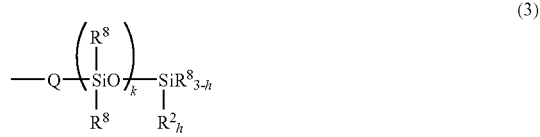

wherein $R^2$ is as defined above, each $R^8$ is, independently, selected from the group consisting of C1-30 alkyl, C1-30 fluoroalkyl, C6-30 aryl, and C6-30 aralkyl groups, Q is $C_dH_{2d}$ or an oxygen atom, wherein d is an integer of from 1 to 5, k is an integer of from 0 to 500, and h is an integer of from 0 to 3, a is a number of from 1.5 to 2.5,
b is a number of from 0.001 to 1.5, and
c is a number of from 0 to 1.5.

The aforesaid organopolysiloxane of the present invention is highly reactive because of terminal carboxyl groups, so that it is useful for applications where high reactivity is required such as surface treatment of powder. The organopolysiloxane has high affinity with unctuous agents and, particularly, the one having $R^3$ has higher affinity with unctuous agents. Surface-treated powder with the organopolysiloxane is highly dispersive in unctuous agent.

DETAILED DESCRIPTION OF THE PREFERRED EMBODIMENTS

In the compositional formula (1), $R^1$ is a group selected from the group consisting of C1-30 alkyl, C1-30 fluoroalkyl, C6-30 aryl and C6-30 aralkyl groups. Examples of $R^1$ include alkyl groups such as methyl, ethyl, propyl, butyl, pentyl, hexyl, heptyl, octyl, nonyl, decyl, and stearyl groups; alicyclic groups such as cyclopentyl and cyclohexyl groups: aryl groups such as phenyl, and tolyl groups; aralkyl groups such as benzyl, and phenetyl groups; and fluoroalkyl groups such as trifluoropropyl and heptadecafluorodecyl groups. Among these, C1-15 alkyl and phenyl groups are preferred, and a methyl group is more preferred.

$R^2$ is represented by the following formula (2):

wherein a $R^4$ is a C2-20, preferably C2-12, divalent hydrocarbon group, which may have an oxygen atom. Examples of $R^4$ include alkylene groups such as ethylene, propylene, hexamethylene, decamethylene, and hexadecamethylene groups; and oxyalkylene groups such as oxyethylene and oxypropylene groups, among which ethylene and propylene groups are preferred.

$R^2$ is bonded to at least one end of the organopolysiloxane. In the organopolysiloxane having $R^3$, $R^2$ may be bonded to an end of the $R^3$ and may be bonded to a site other than the ends of the organopolysiloxane main chain. Preferably, $R^2$ is bonded to an end of the organopolysiloxane main chain, and more preferably there is only one R2 that is bonded to an end of the organopolysiloxane main chain. It is considered, though not to limit the present invention, the terminal $R^2$ allows fast reaction with a surface of substrate such as powder, and the rest part of the organopolysiloxane achieves good affinity with an unctuous agent.

Each of $R^5$ is, independently, a hydrogen atom, a monovalent cation or a C1-10 alkyl group, provided that at least one of $R^5$'s is a hydrogen atom or a monovalent cation. Examples of the monovalent cation include ions of alkali metals such as lithium, sodium, and potassium; ammonium and alkylammonium. Examples of the alkyl group include methyl, ethyl, propyl, and isopropyl groups. Preferably, $R^5$ is a hydrogen atom, a sodium ion or a potassium ion.

$R^6$ is each, independently, a hydrogen atom or a C1-6 alkyl group, and preferably a hydrogen atom or a methyl group. $R^7$ is a hydrogen atom or a C1-6 alkyl group, and preferably a hydrogen atom or a methyl group.

In the formula (1), $R^3$ is a group represented by the following formula (3):

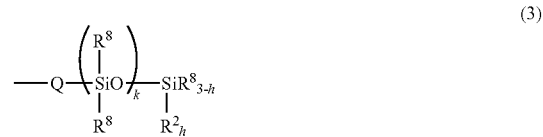

wherein each $R^8$ is, independently, selected from the group consisting of C1-30 alkyl, C1-30 fluoroalkyl, C6-30 aryl, and C6-30 aralkyl groups. Examples of $R^8$ include those aforementioned for $R^1$ among which a methyl group is preferred. Q is $C_dH_{2d}$, wherein d is an integer of from 1 to 5, preferably from 2 to 4, or an oxygen atom, preferably $C_2H_4$. k is an integer of from 0 to 500, preferably from 1 to 100, and more preferably from 5 to 60. h is an integer of from 0 to 3, preferably 0.

In the formula (1), a is a number of from 1.5 to 2.5, preferably from 1.8 to 2.3, b is a number of from 0.001 to 1.5, preferably from 0.01 to 0.5, and more preferably from 0.01 to 0.09, and c is a number of from 0 to 1.5, preferably from 0 to 0.6, more preferably from 0 to 0.3. An organopolysiloxane with b being smaller than the aforementioned lower limit may not have sufficient reactivity and adsorption capability of carboxyl groups. On the other hand, an organopolysiloxane with b and c being greater than 1.5 tends to have a viscosity too high to handle with ease.

An exemplary organopolysiloxane of the present organopolysiloxane is represented by the following formula:

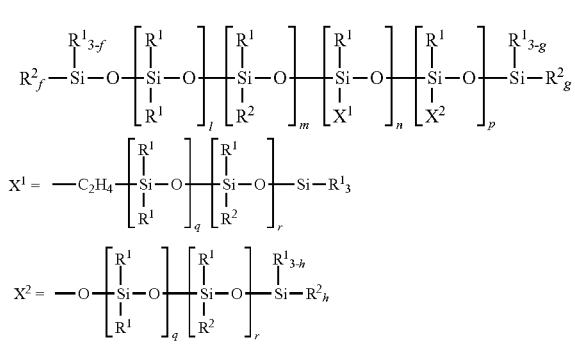

wherein Q and h are as defined above, l is an integer of from 0 to 500, m is an integer of from 0 to 50, n is an integer of from 0 to 50, p is an integer of from 0 to 50, q is an integer of from 0 to 500, r is an integer of from 0 to 50, f and g are integers of from 0 to 3, provided that 1≦f+g. Preferably, l is an integer of from 5 to 60, m is an integer of from 0 to 10, n is an integer of from 1 to 10, p is an integer of from 0 to 10, q is an integer of from 1 to 100, r is an integer of from 0 to 5, f, g and h are 0 or 1, provided that f+g+h is at least one, 5≦l+m≦550. Preferably, l+m ranges from 10 to 300, and q+r ranges from 1 to 100, more preferably from 5 to 60.

The organopolysiloxane having carboxyl groups of the present invention can be prepared by a method comprising the steps of:

(1) subjecting an organohydrogenpolysiloxane having hydrogen atoms at the sites where $R^2$ and $R^3$ are to be bonded and an acid anhydride compound represented by the following formula (4) to an addition reaction,

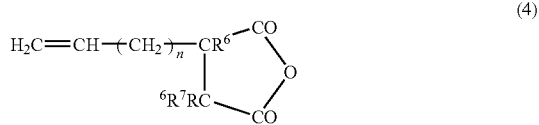

(4)

wherein each $R^6$ is, independently, a hydrogen atom or a C1-6 alkyl group, $R^7$ is a hydrogen atom or a C1-6 alkyl group, and n is an integer of from 0 to 18, and (2) subjecting a product obtained in the step (1) to a ring-opening reaction in the presence of water.

With an additional step (3) reacting a carboxylic acid obtained in the step (2) with an organic or inorganic base, an organopolysiloxane with its proton being replaced with a monovalent cation can be prepared.

The organohydrogenpolysiloxane used in the step (1) can be linear or branched. The branched organohydrogenpolysiloxane is the one having a network structure with a $(R^1SiO_{3/2})$ unit and/or a $(SiO_{4/2})$ unit. A SiH bond is located on at least one end of a main chain of the organohydrogenpolysiloxane. It may be located at an end of a side-chain, if there is a side-chain. It bond may be located at a site other than the ends when there is a silicone side-chain, but preferably at an end.

In the formula (4), $R^6$ and $R^7$ are as defined above and n is an integer of from 0 to 18, preferably from 0 to 10. Examples of the acid anhydride compound include succinic acid anhydride and derivatives thereof such as vinyl succinic acid anhydride, allyl succinic acid anhydride, allyl-2-methylsuccinic acid anhydride, allyl-2,3-dimethyl succinic acid anhydride, and allyl-2-ethyl succinic acid anhydride. Preferably, allyl succinic acid anhydride is used.

The addition reaction in the step (1) is preferably performed in the presence of a platinum or rhodium catalyst. Examples of preferred catalyst include chloroplatinic acid, chloroplatinic acid modified with an alcohol, and a complex of chloroplatinic acid with a vinylsiloxane. An amount of the catalyst to be used may be a catalytically effective amount, i.e., a catalytic amount, which is usually at most 50 ppm, particularly at most 20 ppm, as platinum or rhodium metal. The reaction may be performed in an organic solvent as needed. Examples of the organic solvent include aliphatic alcohols such as methanol, ethanol, 2-propanol and butanol; aromatic hydrocarbons such as toluene and xylene; aliphatic or alicyclic hydrocarbons such as n-pentane, n-hexane, and cyclohexane; and halogenated hydrocarbons such as dichloromethane, chloroform, and carbon tetrachloride. Reaction conditions for the addition reaction are not limited to particular ones. Preferably, the reaction is performed under reflux for 1 to 10 hours.

In the step (1), $R^3$ with Q being $C_dH_{2d}$ and h being 0 can be introduced to the organopolysiloxane by subjecting an organopolysiloxane represented by the following formula (5) having an unsaturated group at an end to an addition reaction in parallel with the addition reaction of the aforesaid acid anhydride.

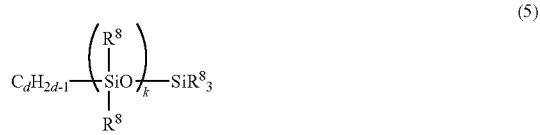

(5)

In the formula (5), $R^8$, k, and d are as defined above. $R^3$ with Q being an oxygen atom can be prepared by forming a siloxane backbone through an equilibration reaction and then reacting the organohydrogenpolysiloxane thus obtained with the aforementioned acid anhydride of the formula (4).

The ring-opening reaction in the step (2) is performed by adding water to reactants according to a conventional method. An amount of water to be added is at least an equivalent molar amount, preferably from two- to five-fold molar amounts, of the acid anhydride group. The reaction may be performed in an organic solvent as needed. Examples of the organic solvent include those listed for the step (1). The reaction conditions for the ring-opening reaction are not limited to the particular ones. Preferably, the reaction is performed at a temperature of from room temperature to a reflux temperature for 1 to 10 hours. A basic catalyst such as an amine or ammonium in an amount of from 1 to 1,000 ppm may be added to promote the ring-opening reaction.

In the ring-opening reaction, use of a C1-10 alcohol or its metal alcoholate in place of water produces an organopolysiloxane with $R^5$ being C1-10 alkyl group in the formula (2).

Examples of the base used in the step (3) include metal hydroxides such as sodium hydroxide and potassium hydroxide, and amines such as ammonia water and trialkylamine. The metal hydroxides can be added in the form of an aqueous solution or alcoholic solution.

The organopolysiloxane of the present invention has a carboxyl equivalent (g/mol) of from 100 to 50000, preferably from 500 to 10000, more preferably from 500 to 5000. For good handling property, the organopolysiloxane preferably has a viscosity of from 10 to 1,000,000 mm$^2$/sec, more preferably from 10 to 100,000 mm$^2$/sec. Further, the organopolysiloxane preferably has a weight average molecular weight reduced to polystyrene of from 200 to 100,000, more preferably from 200 to 50,000. If the weight average molecular weight exceeds 100,000, viscosity becomes too high to handle with ease. On the other hand, an organopolysiloxane having a weight average molecular weight below 200 has too little siloxane units to make the best of the siloxane units.

The organopolysiloxane of the present invention is used for treating surfaces of organic resins, fibers, and powder, preferably powder, to provide the surface with water resistance and affinity with unctuous agents. Examples of the unctuous agents include hydrocarbon, ester, and silicone unctuous agents. Examples of the hydrocarbon unctuous agent include ozokerite, α-olefin oligomer, light isoparaffin, isododecane, isohexadecane, light liquid isoparaffin, squalane, synthetic squalane, plant-origin squalane and squalene, among which isododecane and isohexadecane are preferred.

Examples of the ester unctuous agent include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl. Examples of glyceride oils include acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate, among which isocetyl isostearate, cetyl octanoate, and isononyl isononanate.

Examples of the silicone unctuous agent include linear or branched organopolysiloxanes having low to high viscosities such as dimethylpolysiloxane, tristrimethylsiloxymethylsilane, caprylyl methicone, phenyltrimethicone, tetrakistrimethylsiloxysilane, methylphenylpolysiloxane, methylhexylpolysiloxane, methylhydrogenpolysiloxane, and copolymers of dimethylsiloxane and methylphenylsiloxane; cyclic organopolysiloxanes such as octamethylcyclotetrasiloxane, decamethylcyclopentasiloxane, dodecamethylcyclohexasiloxane, and tetramethyl-tetrahydrogencyclotetrasiloxane; amino-modified oganopolysiloxanes, pyrrolidonyl-modified oganopolysiloxanes, pyrrolidonyl/carboxyl-modified organopolysiloxanes; silicone rubbers such as gummy dimethylpolysiloxanes having high polymerization degrees, gummy amino-modified organopolysiloxanes, and gummy dimethylsiloxane/methylphenylsiloxane copolymers and solutions of silicone rubber in cyclic organopolysiloxane; trimethylsiloxysilicate, and solutions of trimethylsiloxysilicate in cyclic siloxane, higher alkoxy-modified silicones such as stearoxysilicone, higher fatty acid-modified silicones, alkyl-modified silicones, long chain alkyl-modified silicones, amino acid-modified silicones, fluorinated silicones, silicone resins and solutions of silicone resins, among which cyclic organopolysiloxanes such as octamethylcyclotetrasiloxane, decamethylcyclopentasiloxane, dodecamethylcyclohexasiloxane, tetramethyl-tetrahydrogencyclotetrasiloxane, and tetramethyltetraphenylcyclotetrasiloxane are preferred.

The powder to be treated with the organopolysiloxane is not limited to particular ones. Preferred are powder of titanium dioxide, zinc oxide and sericite.

EXAMPLES

The present invention is explained in further detail below with reference to examples, but the present invention is in no way limited by the examples. In the following, "%" means "% by weight" unless otherwise specified.

Example 1

In a reactor, were placed 241 parts by weight of an organohydrogenpolysiloxane represented by the following formula (6):

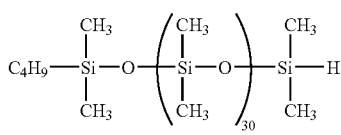

(6)

14.7 parts by weight of ally succinic acid anhydride represented by the following formula (7):

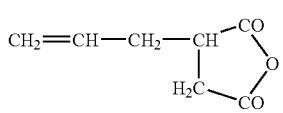

(7)

and 100 parts by weight of toluene, to which 0.1 part of a 0.5 wt % solution of chloroplatinic acid in toluene was added, and then subjected to a reaction under reflux of the solvent for 2 hours. The reaction mixture was then heated at a reduced pressure to remove the solvent, whereby a liquid having a viscosity of 82 mm$^2$/s was obtained with 98% yield. IR and 1H-NMR spectral analyses of the liquid identified it as an organopolysiloxane having acid anhydride groups represented by the following formula (8):

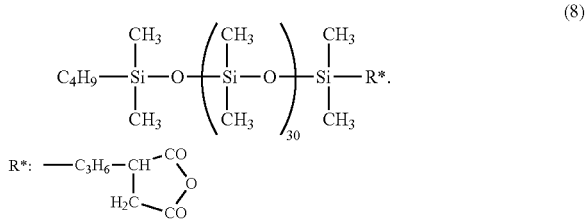

(8)

| IR | $^1$H-NMR (CDCl$_3$) |
|---|---|
| 2963 cm$^{-1}$ (C—H) | 0 ppm (s, 192H, Si—CH$_3$) |
| 1867 cm$^{-1}$ (C=O) | 0.5 ppm (t, 2H, Si—CH$_2$) |
| 1790 cm$^{-1}$ (C=O) | 0.9 ppm (t, 3H, C—CH$_3$) |
| 1260 cm$^{-1}$ (Si—CH$_3$) | 1.3 ppm (m, 4H, C—CH$_2$) |
| 1100 to 1020 cm$^{-1}$ (Si—O) | 1.4 ppm (m, 2H, C—CH$_2$) |
| | 1.8 ppm (m, 2H, C—CH$_2$) |
| | 2.6 ppm (m, 1H, CH—CO) |
| | 3.1 ppm (m, 2H, CH$_2$—CO) |

To 250 parts by weight of the above organopolysiloxane having acid anhydride groups, 100 parts by weight of tetrahydrofuran and 5.4 parts by weight of water were added, which were then subjected to a reaction under reflux for 5 hours. The reaction mixture was subjected to vacuum distillation, whereby a liquid having a viscosity of 147 mm$^2$/s and a carboxyl equivalent of 1290 g/mol was obtained with 97% yield. IR and 1H-NMR spectral analyses of the liquid identified it as an organopolysiloxane having carboxyl groups represented by the following formula (9):

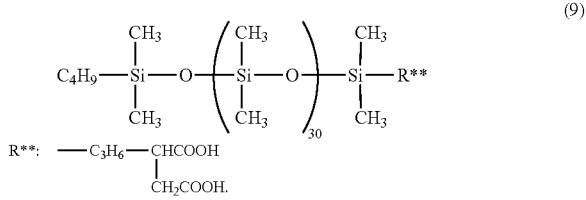

(9)

| IR | $^1$H-NMR (CDCl$_3$) |
|---|---|
| 3300 to 2500 cm$^{-1}$ (—OH) | 0 ppm (s, 189H, Si—CH$_3$) |
| 2965 cm$^{-1}$ (C—H) | 0.5 ppm (t, 6H, Si—CH$_2$) |
| 1716 cm$^{-1}$ (C=O) | 1.4 ppm (m, 6H, C—CH$_2$) |
| 1260 cm$^{-1}$ (Si—CH$_3$) | 1.8 ppm (m, 6H, C—CH$_2$) |
| 1100 to 1020 cm$^{-1}$ (Si—O) | 2.5 ppm (m, 3H, CH—CO) |
| | 2.8 ppm (m, 6H, CH$_2$—CO) |
| | 11.5 ppm (s, 2H, —COOH) |

Reference Example 2

In a reactor, were placed 240 parts by weight of an organohydrogenpolysiloxane represented by the following formula (10):

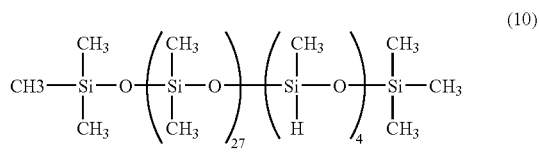

28.0 parts by weight of ally succinic acid anhydride, and 168 parts by weight of an organopolysiloxane having a vinyl group at an end represented by the following formula (11):

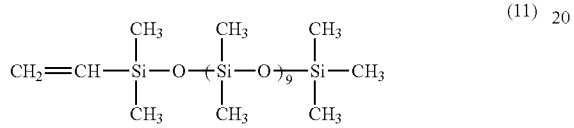

and 100 parts by weight of toluene, to which 0.1 part of a 0.5 wt % solution of chloroplatinic acid in toluene was added, and then subjected to a reaction under reflux of the solvent for 2 hours. The reaction mixture was then heated at a reduced pressure to remove the solvent, whereby a liquid having a viscosity of 110 mm²/s was obtained with 98% yield. IR and ¹H-NMR spectral analyses of the liquid identified it as an organopolysiloxane having acid anhydride groups represented by the following formula (12):

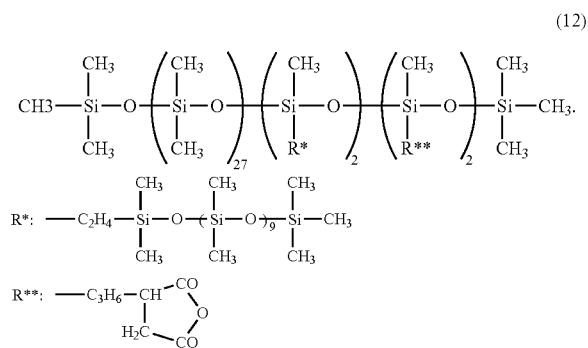

| IR | ¹H-NMR (CDCl₃) |
|---|---|
| 2963 cm⁻¹ (C—H) | 0 ppm (s, 330H, Si—CH₃) |
| 1867 cm⁻¹ (C=O) | 0.4 ppm (m, 8H, Si—CH₂) |
| 1790 cm⁻¹ (C=O) | 0.5 ppm (t, 4H, Si—CH₂) |
| 1260 cm⁻¹ (Si—CH₃), 1100 to 1020 cm⁻¹ (Si—O) | 1.4 ppm (m, 4H, C—CH₂) |
| | 1.7 ppm (m, 4H, C—CH₂) |
| | 2.4 ppm (m, 2H, CH—CO) |
| | 2.8 ppm (m, 4H, CH₂—CO) |

To 250 parts by weight of the above organopolysiloxane having acid anhydride groups, 100 parts by weight of tetrahydrofuran and 7.2 parts by weight of water were added, which were then subjected to a reaction under reflux for 5 hours The reaction mixture was subjected to vacuum distillation, whereby a liquid having a viscosity of 850 mm²/s and a carboxyl equivalent of 1110 g/mol was obtained with 95% yield. IR and ¹H-NMR spectral analyses of the liquid identified it as an organopolysiloxane having carboxyl groups represented by the following formula (13):

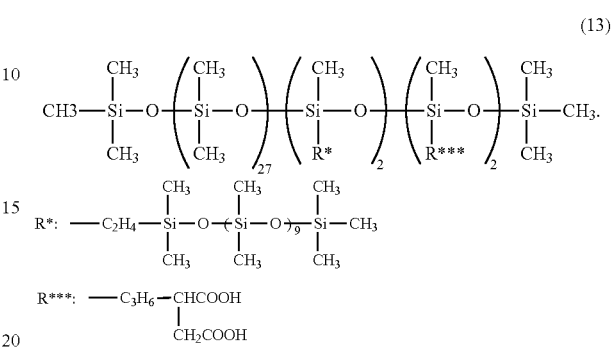

| IR | ¹H-NMR (CDCl₃) |
|---|---|
| 3300 to 2500 cm⁻¹ (—OH) | 0 ppm (s, 330H, Si—CH₃) |
| 2965 cm⁻¹ (C—H) | 0.4 ppm (m, 8H, Si—CH₂) 0.5 ppm (t, 4H, Si—CH₂) |
| 1715 cm⁻¹ (C=O) | |
| 1260 cm⁻¹ (Si—CH₃) | 1.4 ppm (m, 4H, C—CH₂) |
| 1100 to 1020 cm⁻¹ (Si—O) | 1.7 ppm (m, 4H, C—CH₂) |
| | 2.4 ppm (m, 2H, CH—CO) |
| | 2.8 ppm (m, 4H, CH₂—CO) 11.0 ppm (s, 4H, COOH) |

Comparative Example 1

In a reactor, were placed 228 parts by weight of an organohydrogenpolysiloxane represented by the following formula (14):

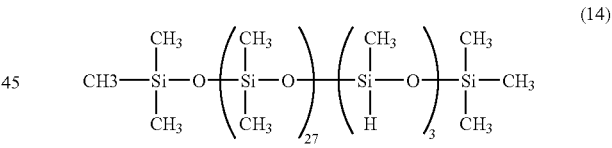

29.4 parts by weight of ally succinic acid anhydride and 100 parts by weight of toluene, to which 0.1 part of a 0.5 wt % solution of chloroplatinic acid in toluene was added, and then subjected to a reaction under reflux of the solvent for 2 hours. The reaction mixture was then heated at a reduced pressure to remove the solvent, whereby a liquid having a viscosity of 84 mm²/s was obtained with 98% yield. IR and ¹H-NMR spectral analyses of the liquid identified it as an organopolysiloxane having acid anhydride groups represented by the following formula (15):

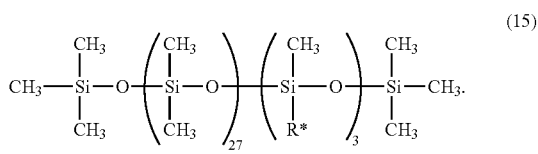

-continued

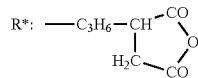

| IR | $^1$H-NMR (CDCl$_3$) |
|---|---|
| 2963 cm$^{-1}$ (C—H) | 0 ppm (s, 189H, Si—CH$_3$) |
| 1867 cm$^{-1}$ (C=O) | 0.5 ppm (t, 6H, Si—CH$_2$) |
| 1790 cm$^{-1}$ (C=O) | 1.4 ppm (m, 6H, C—CH$_2$) |
| 1260 cm$^{-1}$ (Si—CH$_3$) | 1.8 ppm (m, 6H, C—CH$_2$) |
| 1100 to 1020 cm$^{-1}$ (Si—O) | 2.6 ppm (m, 3H, CH—CO) |
|  | 3.1 ppm (m, 6H, CH$_2$—CO) |

To 250 parts by weight of the above organopolysiloxane having acid anhydride groups, 100 parts by weight of tetrahydrofuran and 7.2 parts by weight of water were added, which were then subjected to a reaction under reflux for 5 hours. The reaction mixture was subjected to vacuum distillation, whereby a liquid having a viscosity of 8700 mm$^2$/s and a carboxyl equivalent of 435 g/mol was obtained with 97% yield. IR and $^1$H-NMR spectral analyses of the liquid identified it as an organopolysiloxane having carboxyl groups represented by the following formula (16):

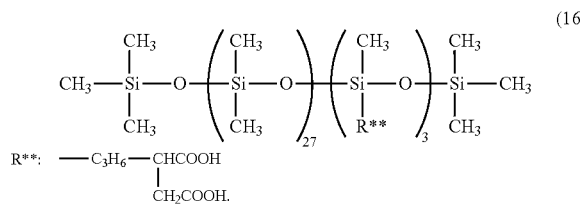

(16)

| IR | $^1$H-NMR (CDCl$_3$) |
|---|---|
| 3300 to 2500 cm$^{-1}$ (—OH) | 0 ppm (s, 189H, Si—CH$_3$) |
| 2963 cm$^{-1}$ (C—H) | 1.5 ppm (t, 6H, Si—CH$_2$) |
| 1716 cm$^{-1}$ (C=O) | 1.4 ppm (m, 6H, C—CH$_2$) |
| 1260 cm$^{-1}$ (Si—CH$_3$) | 1.8 ppm (m, 6H, C—CH$_2$) |
| 1100 to 1020 cm$^{-1}$ (Si—O) | 2.5 ppm (m, 3H, CH—CO) |
|  | 2.8 ppm (m, 6H, CH$_2$—CO) |
|  | 11.3 ppm (s, 6H, —COOH) |

Comparative Example 2

In a reactor, were placed 266 parts by weight of an organohydrogenpolysiloxane represented by the following formula (17):

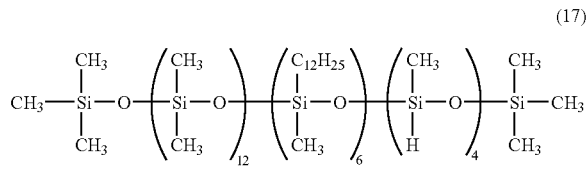

(17)

58.8 parts by weight of ally succinic acid anhydride and 100 parts by weight of toluene, to which 0.1 part of a 0.5 wt % solution of chloroplatinic acid in toluene was added, and then subjected to a reaction under reflux of the solvent for 2 hours. The reaction mixture was then heated at a reduced pressure to remove the solvent, whereby a liquid having a viscosity of 145 mm$^2$/s was obtained with 97% yield. IR and $^1$H-NMR spectral analyses of the liquid identified it as an organopolysiloxane having acid anhydride groups represented by the following formula (18):

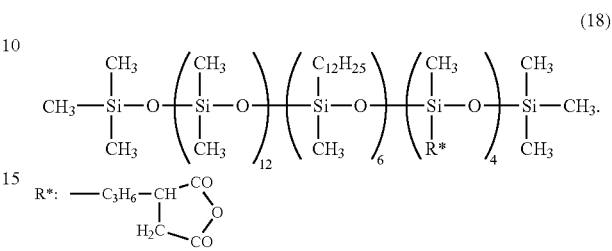

(18)

| IR | $^1$H-NMR (CDCl$_3$) |
|---|---|
| 2965, 2925, 2856 cm$^{-1}$ (C—H) | 0 ppm (s, 120H, Si—CH$_3$) |
| 1867 cm$^{-1}$ (C=O) | 0.5 ppm (m, 20H, Si—CH$_2$) |
| 1790 cm$^{-1}$ (C=O) | 0.9 ppm (t, 18H, C—CH$_3$) |
| 1260 cm$^{-1}$ (Si—CH$_3$) | 1.3 ppm (m, 120H, C—CH$_2$) |
| 1100 to 1020 cm$^{-1}$ (Si—O) | 1.4 ppm (m, 8H, C—CH$_2$) |
|  | 1.8 ppm (m, 8H, C—CH$_2$) |
|  | 2.6 ppm (m, 4H, CH—CO) |
|  | 3.1 ppm (m, 8H, CH$_2$—CO) |

To 250 parts by weight of the above organopolysiloxane having acid anhydride groups, 100 parts by weight of tetrahydrofuran and 14.4 parts by weight of water were added, which were then subjected to a reaction under reflux for 5 hours. The reaction mixture was subjected to vacuum distillation, whereby a liquid having a viscosity of 9800 mm$^2$/s and a carboxyl equivalent of 415 g/mol was obtained with 96% yield. IR and $^1$H-NMR spectral analyses of the liquid identified it as an organopolysiloxane having carboxyl groups represented by the following formula (19):

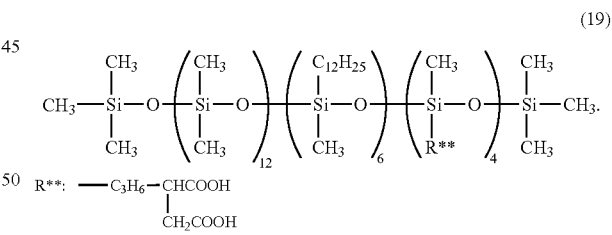

(19)

| IR | $^1$H-NMR (CDCl$_3$) |
|---|---|
| 3300 to 2500 cm$^{-1}$ (—OH) | 0 ppm (s, 120H, Si—CH$_3$) |
| 2965, 2925, 2856 cm$^{-1}$ (C—H) | 0.5 ppm (t, 20H, Si—CH$_2$) |
| 1715 cm$^{-1}$ (C=O) | 0.9 ppm (t, 18H, C—CH$_3$) |
| 1260 cm$^{-1}$ (Si—CH$_3$) | 1.3 ppm (m, 120H, C—CH$_2$) |
| 1100 to 1020 cm$^{-1}$ (Si—O) | 1.4 ppm (m, 8H, C—CH$_2$) |
|  | 1.8 ppm (m, 8H, C—CH$_2$) |
|  | 2.5 ppm (m, 4H, CH—CO) |
|  | 2.8 ppm (m, 8H, CH$_2$—CO) |
|  | 11.4 ppm (s, 8H, —COOH) |

<Powder Treatment>

Powder of titanium dioxide or zinc oxide was treated with the organopolysiloxanes obtained in the above Examples, Comparative Examples, and a surface treatment agent (Comparative example 3), respectively, according to the formulation shown in the following Table. In a reactor, 98 parts by weight of titanium dioxide or zinc oxide powder, which had not been surface-treated and dried under vacuum, were placed, to which a solution of an organopolysiloxane dissolved in about 100 parts by weight of toluene was gradually added while stirring the powder. A temperature of the reactor was raised from room temperature to about 120° C. to remove toluene, and then to 150° C. at which temperature the powder was stirred for 3 hours.

TABLE 1

| Surface-treated powder | Powder, parts by weight | | Organopolysiloxane, parts by weight | | | | |
|---|---|---|---|---|---|---|---|
| | Titanium dioxide | Zinc oxide | Ex. 1 | Ex. 2 | Com. Ex. 1 | Comp. Ex. 2 | Comp. Ex. 3 |
| 1 | 98 | | 2 | | | | |
| 2 | 98 | | | 2 | | | |
| 3 | | 98 | 2 | | | | |
| 4 | | 98 | | 2 | | | |
| 5 | 98 | | | | 2 | | |
| 6 | 98 | | | | | 2 | |
| 7 | 98 | | | | | | 2 |
| 8 | | 98 | | | 2 | | |
| 9 | | 98 | | | | 2 | |
| 10 | | 98 | | | | | 2 |

Surface treatment agent used in Comparative Example 3: An organopolysiloxane having carboxyl groups represented by the following formula:

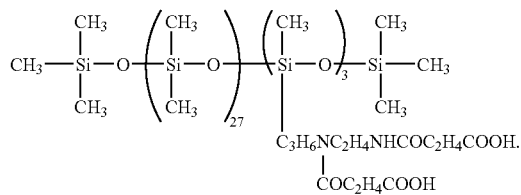

<Stability of Dispersion>

Dispersions of the surface-treated powders were prepared. In 50 ml of isododecane, 2.5 g of each surface-treated powder was dispersed with a bead mill. The dispersion obtained was transferred to a 50-ml test tube. The dispersion in the test tube was left standing for 2 days, and then visually observed for sedimentation of the powder. As references, dispersions of titanium dioxide powder and zinc oxide powder which had not been surface-treated were prepared in the same manner. Results are shown in the following Table 2. In the Table, values in the second column indicate a height of the uppermost powder after 2 day-standing relative to an initial height, that is, "1.0" indicates no sedimentation. A smaller value indicates a larger degree of sedimentation.

TABLE 2

| Surface-treated powder | Stability of dispersion |
|---|---|
| 1 | 1.0 |
| 2 | 1.0 |
| 3 | 1.0 |
| 4 | 0.9 |
| 5 | 0.7 |
| 6 | 0.8 |
| 7 | 0.5 |
| 8 | 0.8 |
| 9 | 0.7 |
| 10 | 0.6 |
| Non-treated titanium dioxide | 0.2 |
| Non-treated zinc oxide | 0.2 |

As shown in Table 2, powders treated with the organopolysiloxanes of the Examples hardly settled down, indicating good dispersivity. In contrast, the powders treated with the organopolysiloxane which does not have terminal carboxyl groups or a silicone side-chain showed sedimentation. Particularly, Comparative Example 3 showed significant sedimentation.

INDUSTRIAL APPLICABILITY

The organopolysiloxane of the present invention, because of characteristics of carboxyl groups, is suitable for modifying organic resins or fibers and surface-treating powder. The treated surface shows high affinity with an unctuous agent. Particularly, dispersivity of powder is significantly improved. The organopolysiloxane, therefore, is useful for applications where high dispersivity of powder is required, for example, cosmetics such as skincare and makeup products, and coatings.

What is claimed is:

1. An organopolysiloxane represented by the following formula:

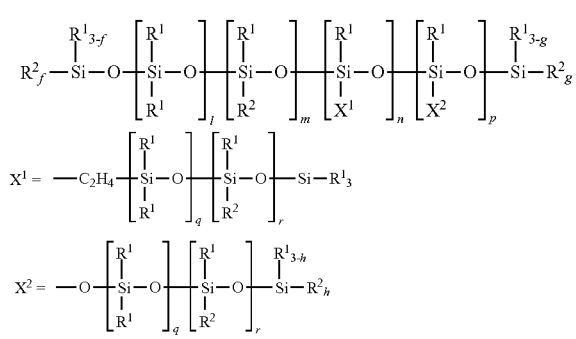

wherein $R^1$ is selected from the group consisting of C1-30 alkyl, C1-30 fluoroalkyl, C6-30 aryl, and C6-30 aralkyl groups, $R^2$ is a group represented by the following formula (2):

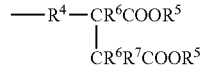

(2)

wherein $R^4$ is a C2-20 divalent hydrocarbon group which has an oxygen atom or no oxygen atom, each $R^5$ is, independently, a hydrogen atom, a monovalent cation, or a C1-10 alkyl group, provided that at least one of $R^5$'s is a hydrogen atom or a monovalent cation, each $R^6$ is, independently, a hydrogen atom or a C1-6 alkyl group, and $R^7$ is a hydrogen atom or a C1-6 alkyl group, l is an integer of from 5 to 500,
m is an integer of from 0 to 50,
n is an integer of from 0 to 50,
p is an integer of from 0 to 50,
q is an integer of from 0 to 500,
r is an integer of from 0 to 50,
f and g are integers of from 0 to 3 provided that $1 \leq f+g$, and
h is an integer of from 0 to 3.

2. The organopolysiloxane according to claim 1, wherein each $R^5$ is, independently, a hydrogen atom, a sodium ion or a potassium ion.

3. The organopolysiloxane according to claim 1, wherein $R^6$ and $R^7$ are hydrogen atoms.

4. The organopolysiloxane according to claim 1, wherein m is 0 and f+g=1.

5. A surface treatment agent for a powder, said surface treatment agent comprising an organopolysiloxane according to any one of claims 1 to 3 or 4.

6. The surface treatment agent according to claim 5, wherein the powder is selected from the group consisting of titanium dioxide, zinc oxide, and sericite.

7. The surface treatment agent according to claim 5, wherein said agent comprises said organopolysiloxane dissolved in toluene.

* * * * *